US006261405B1

(12) United States Patent
Laprade

(10) Patent No.: US 6,261,405 B1
(45) Date of Patent: Jul. 17, 2001

(54) METHOD AND APPARATUS FOR MAKING A PATCH

(75) Inventor: Ronald E. Laprade, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/104,538

(22) Filed: Jun. 26, 1998

Related U.S. Application Data

(60) Provisional application No. 60/051,057, filed on Jun. 27, 1997.

(51) Int. Cl.[7] .................................................. B32B 31/00
(52) U.S. Cl. ....................... 156/324; 156/229; 156/359; 156/494; 156/498
(58) Field of Search .......................... 156/229, 359, 156/494, 498, 555, 324

(56) References Cited

U.S. PATENT DOCUMENTS

| | | | |
|---|---|---|---|
| Re. 32,991 | 7/1989 | Szycher et al. ............... | 528/75 |
| 4,093,499 | * 6/1978 | Naka ............................ | 156/498 |
| 4,306,551 | 12/1981 | Hymes et al. ................ | 128/156 |
| 4,307,717 | 12/1981 | Hymes et al. ................ | 128/156 |
| 4,512,838 | * 4/1985 | Rausing ....................... | 156/203 |
| 4,556,441 | 12/1985 | Faasse, Jr. ................... | 156/247 |
| 4,675,009 | 6/1987 | Hymes et al. ................ | 604/304 |
| 4,853,063 | * 8/1989 | Basgil et al. ................. | 156/238 |
| 4,915,102 | 4/1990 | Kwiatek et al. ............. | 128/156 |
| 5,123,900 | 6/1992 | Wick ............................. | 602/41 |
| 5,183,664 | 2/1993 | Ansell ........................... | 424/445 |
| 5,268,179 | 12/1993 | Rudella ........................ | 424/449 |
| 5,350,581 | 9/1994 | Kochinke ..................... | 424/443 |
| 5,370,924 | 12/1994 | Kochinke ..................... | 428/224 |
| 5,503,844 | 4/1996 | Kwiatek et al. ............. | 424/449 |
| 5,505,958 | 4/1996 | Bello et al. .................. | 424/449 |
| 5,518,734 | 5/1996 | Stefano et al. ............... | 424/448 |
| 5,536,263 | 7/1996 | Rolf et al. .................... | 604/307 |
| 5,571,079 | 11/1996 | Bello et al. .................. | 602/46 |
| 5,629,014 | 5/1997 | Kwiatek et al. ............. | 424/449 |
| 5,635,201 | 6/1997 | Fabo ............................. | 424/443 |
| 5,716,621 | 2/1998 | Bello et al. .................. | 424/443 |
| 5,741,510 | 4/1998 | Rolf et al. .................... | 424/448 |
| 5,824,178 | * 10/1998 | Shingu et al. ................ | 156/265 |

FOREIGN PATENT DOCUMENTS

| | | |
|---|---|---|
| 0 563 507 A1 | 8/1992 | (EP). |
| 0 566 816 A1 | 10/1992 | (EP). |

OTHER PUBLICATIONS

Natus Corp., "Natus Patch," 2 pages plus patch, 1995.

\* cited by examiner

Primary Examiner—James Sells
(74) Attorney, Agent, or Firm—Jay G. Kolman, Esq.

(57) ABSTRACT

A method and apparatus for making a patch comprising a foam supplier for supplying a foam backing having a predetermined porosity, a dispensing device for applying an ointment to the foam backing in a predetermined pattern, and a cooling device for cooling the foam backing prior to application of the ointment, wherein the ointment thickens and cures upon contact with the cooled foam backing.

30 Claims, 2 Drawing Sheets

METHOD AND APPARATUS FOR MAKING A PATCH

In accordance with 35 U.S.C. § 119(e), the benefit of provisional application Ser. No. 60/051,057, filed Jun. 27, 1997, is hereby claimed. The entire contents of this provisional application are incorporated herein by reference.

FIELD OF THE INVENTION

This invention relates to an improved method of making a patch to be applied to the skin. This invention further relates to an apparatus for making a patch.

BACKGROUND OF THE INVENTION

Many variations of patches have been used for applying medication topically, either for local or systematic effect. For example, U.S. Pat. No. 5,536,263 describes a non-occlusive medication patch to be applied to the skin including a porous self-supporting backing layer and a flexible hydrophilic pressure-sensitive adhesive reservoir comprising a hydrocolloid for sustained release of medication to be absorbed topically through the skin. U.S. Pat. No. 5,536,263 teaches that the porosity of the backing layer is important because it provides openings for receiving the medication-containing hydrocolloid reservoir and helps to assure that the patch is non-occlusive. Further, the infusion of the hydrocolloid medication-containing reservoir into the backing sheet is accomplished by controlling manufacturing parameters to keep the hydrocolloid sufficiently fluid to penetrate the backing sheet despite its tendency to thicken rapidly when applied. In order to prevent the hydrocolloid from becoming too viscous to penetrate the backing sheet, the device which applies the hydrocolloid is chilled to remove heat and to keep the hydrocolloid cool. Therefore, U.S. Pat. No. 5,536,263 teaches cooling an application device to lower viscosity of a medication-containing hydrocolloid within the device.

U.S. Pat. No. 5,635,201 discloses a method and apparatus for manufacturing a wound dressing. The method includes coating an upper surface of a perforated carrier material with a curable silicone mixture, blowing cold air onto the underside of the carrier material, and applying heat to the silicone mixture until it is cured to a silicone gel. The cold air is applied by an air blowing unit to remove an applied silicone mixture from perforations in the carrier material, thereby maintaining the porosity of the wound dressing. The cold air further prevents the silicone mixture from curing before it has time to spread over the carrier material. Thus, U.S. Pat. No. 5,635,201 teaches cooling a silicone mixture applied to a carrier strip to prevent curing of the silicone mixture.

One problem that occurs when manufacturing patches, and in particular non-occlusive patches, is undesired spreading of medication-containing ointment when the ointment is heated to a low viscosity for application to a porous backing sheet of a patch. Ointments are not water/solid emulsions and therefore have different properties than a hydrogel and react in a different manner than a hydrogel when heated and cooled. The term "ointment" as used in this application is used in a conventional sense in pharmacy and refers to a material that is semi-solid at room temperatures and softens, but not necessarily melts, at higher temperatures (e.g., when applied to the skin). The term medication is used in the sense of any bioactive agent.

Since an applied ointment fills the pores of a porous backing sheet in the area over which it is spread, the greater the surface area covered by the ointment, the less porous the backing sheet. A less porous backing sheet is undesirable because it makes the patch more occlusive and allows less moisture evaporation from the patient's skin. Lessening moisture evaporation can cause accumulation of water and could cause the patch to fall off. In addition, accumulation of water could cause the growth of bacteria beneath the patch and patient discomfort.

Increased heating of the medication-containing ointment lowers the viscosity of the ointment and thereby increases flow rate of the ointment through an ointment dispenser. Increased flow rate through the ointment dispenser can allow increased production speed and therefore a greater patch yield. However, increased heating of the ointment also increases undesired spreading of the ointment and decreases porosity as described above.

The problems identified above are not intended to be exhaustive but are among the many that reduce the effectiveness of current solutions to the problem of applying medication-containing ointment to a porous backing layer without decreasing porosity of the porous backing layer beyond a desired level; however, the problems presented above should be sufficient to demonstrate that currently known solutions are amenable to worthwhile improvement.

SUMMARY OF THE INVENTION

Accordingly, it would be desirable to provide an apparatus for making a non-occlusive patch which prevents unwanted spreading of a heated medication-containing ointment when the ointment is applied to a porous backing.

It would also be desirable to provide an apparatus for making a non-occlusive patch which prevents unwanted spreading of a heated medication-containing ointment using a low-cost enhancement of standard patch-making components.

It would also be desirable to provide a method of making a non-occlusive patch which prevents unwanted spreading of a heated medication-containing ointment, when the ointment is applied to a porous backing, using a simple procedure.

The present invention provides an apparatus for making a patch comprising a foam supplier for supplying a foam backing having a predetermined porosity; a dispensing device for applying an ointment to the foam backing in a predetermined pattern; and a cooling device for cooling the foam backing prior to application of the ointment, wherein the ointment thickens and cures upon contact with the cooled foam backing.

The present invention also provides a method of making a patch comprising the steps of providing a foam backing having a predetermined porosity; applying an ointment to the foam backing in a predetermined pattern; and cooling the foam backing prior to application of the ointment to increase thickening and curing of the applied ointment upon contact of the applied ointment with the cooled foam backing.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENT

Figure 1:
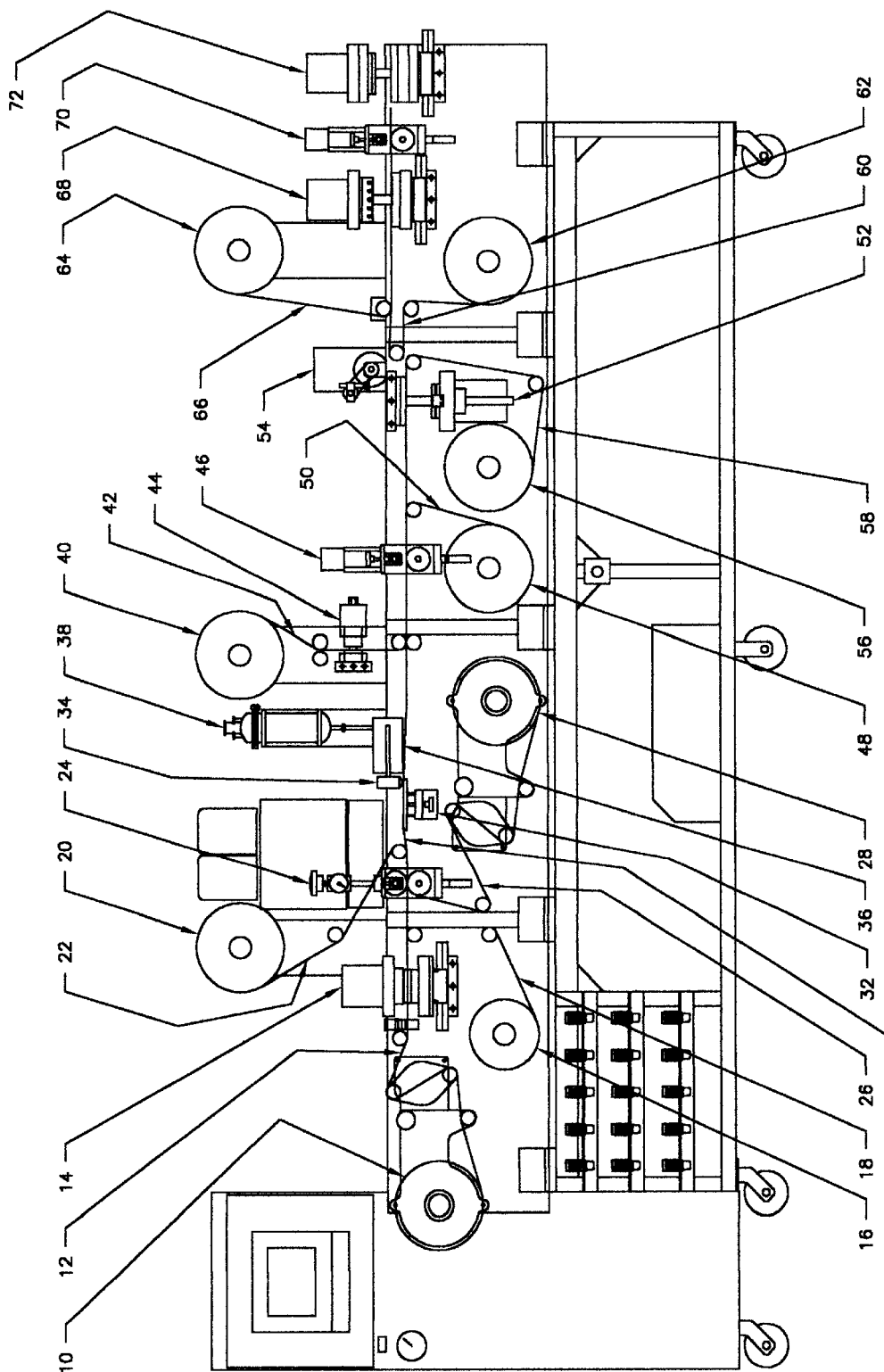
FIG. 1 is a schematic side view of the apparatus for making a non-occlusive patch provided by the invention.

In the figures, like numerals indicate like parts. FIG. 1 shows an improved apparatus for making a non-occlusive patch. In the apparatus, a double sided adhesive unwind 10 can consist of, for example, a constant tension unwind with an adjustable spring loaded dancer arm for adjusting the tension level. The double sided adhesive unwind 10 feeds a double sided adhesive 12 to a center cut-out punch die station 14. Preferably, a web stop air cylinder is used to control registration of the double sided adhesive into the center cutout punch die station 14. The center cut-out punch die station 14 cuts out a predetermined area inside the double-sided adhesive 12 for receiving a medication-containing ointment. The center cut-out punch die station 14 can be operated with, for example, a pneumatic cylinder equipped with a rode guided counter lever section for mounting top and bottom halves of the die.

A bottom adhesive backing rewind 16 takes up a bottom release liner 18 of the double sided adhesive 12 with controlled tension as the bottom-exposed adhesive of the double sided adhesive 12 is fed to a pressure roll station 24.

The pressure roll station 24 laminates the bottom-exposed adhesive of the double sided adhesive 12 to a foam backing 26 at a predetermined laminator nip roll pressure. The pressure roll station 24 can be driven, for example, by a servo motor or by the foam web. After the bottom-exposed adhesive of the double sided adhesive 12 has been laminated to the foam backing 26, a top adhesive backing rewind 20 takes up the top release liner 22 of the double sided adhesive 12 with controlled tension. The foam backing 26 is supplied to the pressure roll station 24 by a foam backing unwind 28. The foam backing unwind 28 may consist of, for example, a constant tension unwind with an adjustable spring loaded dancer arm for adjusting the tension level.

The laminated foam backing 30 is then fed to a cooling device 32 positioned just before a dispensing die 34. The cooling device 32 may comprise, for example, a cooling plate which lies below the laminated foam backing 30 and provides cooling by pumping chilled water or other cooling media through an aluminum plate. A stream of Nitrogen or any other inert gas directed through a manifold positioned adjacent, above, beneath or around the laminated foam backing 30 could also be used either in conjunction with a cooling plate or separately. Other possible embodiments of the cooling device 32 include an air blower provided above, below or around the laminated foam backing 30 to supply cool air, a refrigeration unit through which the laminated foam backing 30 is fed, or any other like means of cooling the laminated foam backing 30.

The dispensing die 34 dispenses medication-containing ointment through, for example, a predetermined slot pattern in a dispensing head. The dispensing die 34 may be used, for example, in conjunction with an IVEK metering pump 36 having a temperature control system to dispense a controlled pattern of medication-containing ointment onto the laminated foam backing 30 within the cut-out section of the double sided adhesive now laminated to the foam backing. The exact location of the ointment may be controlled by, for example, a predetermined program written for a programmable controller.

Before being dispensed by the dispensing die 34, the medication-containing ointment is heated to a desired viscosity, for example to a temperature of between 55 and 65 degrees Celsius by a blend hopper 38 to decrease viscosity of the ointment. This decreased viscosity enables the dispensing die 34 to dispense an accurate and controlled amount of medication-containing ointment through the predetermined slot pattern onto the laminated foam backing 30.

The cooling device 32 pre-cools the laminated foam backing 30 to help prevent undesired spreading of the medication-containing ointment and to control the ointment pattern on the laminated foam backing 30.

The cooling plate may be provided with, for example, a vertical adjuster to adjust the height of the laminated foam backing 30 in relation to the dispensing head of the dispensing die 34. Adjustment of the foam backing height in relation to the dispensing head allows for further control of the pattern of medication-containing ointment dispensed onto the laminated foam backing 30 and further prevents undesired spreading of the ointment.

Figure 2:
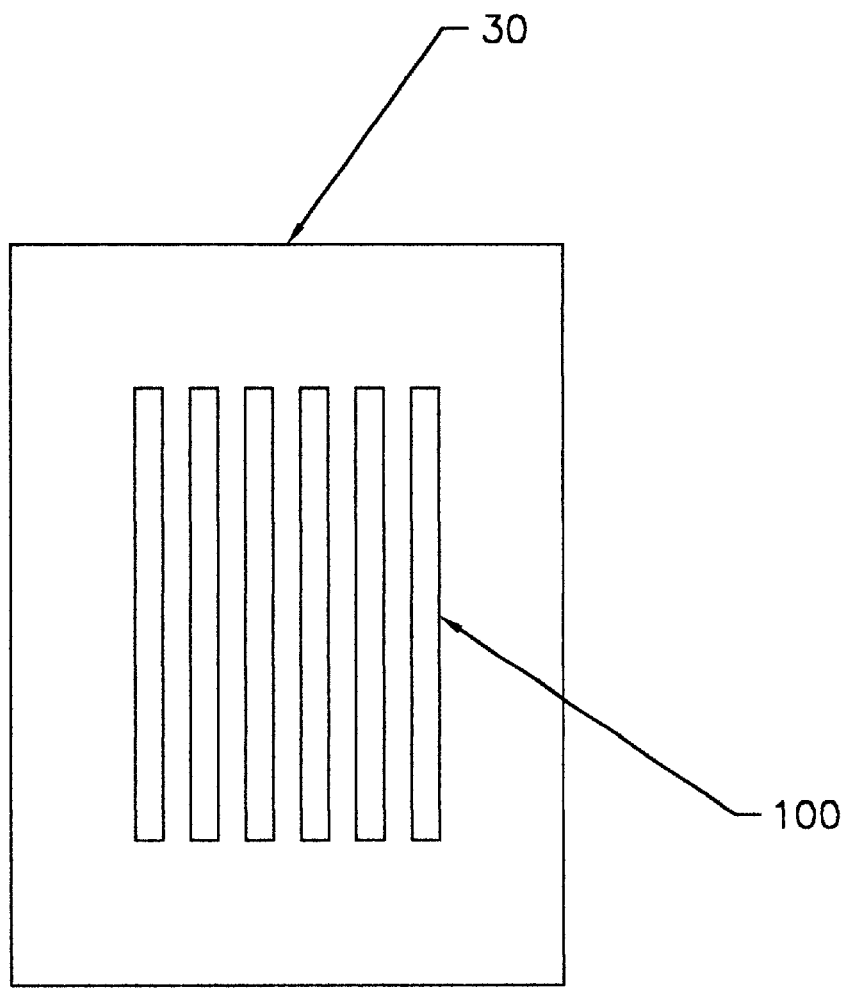
FIG. 2 is a top view of a porous backing sheet with medication-containing ointment applied thereto by the apparatus of the present invention.

As can be seen in FIG. 2, one embodiment of the ointment pattern can be plural lines 100 of droplets of ointment dispensed by the slots of the dispensing head onto the laminated foam backing 30. Any number of lines may be used, and the droplet thickness may vary depending on the desired amount of medication to be applied. The droplets may be applied with little or no gap between successive droplets. The lines of droplets may further be cross-hatched. Other possible shapes could be circles, a series of concentric circles, ovals, etc. It must be recognized, though, that whatever predetermined pattern is chosen for application of the medication-containing ointment, a minimal surface area should be covered by the medication-containing ointment to maintain a high porosity of the foam backing and therefore avoid occlusiveness of the patch in order to decrease moisture build-up under the resulting patch and therefore increase patient comfort and safety from bacteria, and ensure patch adhesiveness.

When the foam backing is cooled, the temperature of the dispensed medication-containing ointment is decreased upon contacting the foam backing 30 and therefore the viscosity of the dispensed medication-containing ointment is increased. Increasing viscosity of the ointment decreases spreading of the ointment over the surface area of the foam backing 30. Upon contacting the cooled foam backing 30, the outer sides of the dispensed medication-containing ointment are cured and therefore spreading of the ointment over the surface area of the foam backing 30 is further decreased. Decreased spreading helps maintain a maximum porosity of the foam backing 30, and therefore precludes occlusiveness of the patch in order to increase patient comfort and safety from bacteria, and ensure patch adhesiveness.

The blend hopper 38 is provided for maintaining the medication-containing ointment at a controlled temperature and supplying the medication-containing ointment to the IVEK metering pump 36. A top cap of the blend hopper 38 may be provided with a port (not shown) for charging ointment to the blend hopper 38.

After the medication-containing ointment has been dispersed onto the laminated foam backing 30 by the dispensing die 34, the laminated foam backing 30 is led to a backing unwind 40 that provides a release liner 42 at a controlled tension for covering the area of dispensed medication-containing ointment on the laminated foam backing 30. Slight pressure is provided to help adhere the release liner 42 to the laminated adhesive on the foam backing 30. The release liner may comprise, for example, silicon.

Prior to applying pressure to adhere the release liner 42 to the laminated foam backing 30, a tear notch is cut into the release liner 42 using a tear notch station 44. The tear notch station 44 consists of a blade mounted at a 45 degree angle to the release liner 42. The tear notch station 44 may be operated, for example, with a pneumatic cylinder equipped with a rod-guided counter-lever section for holding the tear notch blade.

After application of the release liner 42, the laminated foam backing 30 is led to a patch drive station 46. The patch drive station 46 pulls the laminated foam backing, which at this point includes the applied medication-containing ointment and the release liner, through a packaging machine. The driving force may be provided, for example, by rubber drive rolls positioned to lie on either side of the laminated foam backing 30.

After the laminated foam backing 30 passes through the patch drive station 46, a foam backing liner rewind 48 pulls a paper liner 50 from the laminated foam backing 30 at a constant tension which may be provided, for example, by a pneumatic break clutch.

After removal of the paper liner 50, the laminated foam backing 30 is led to a unit die cut station 52. The unit die cut station 52 cuts a finished unit out of the laminated foam backing, which at this point includes the applied medication-containing ointment and the release liner. The unit die cut station 52 comprises a male part of the die and a female part of the die. The male part of the unit die 52 cuts the unit from the bottom to introduce the unit to a pick and place station 54. The unit die cut station 52 may be operated with, for example, a pneumatic cylinder equipped with a rod-guided counter-levered section for holding the male and female parts of the die.

Prior to introduction to the pick and place station 54, a scrap rewind 56 takes up an unused portion 58 of the foam web at a constant tension. The scrap rewind 56 maintains the foam web position at the unit die cut station 52 prior to and after the unit is die cut from the foam web.

The pick and place station 54 picks the die cut unit from the top of the male part of the die and transfers it to a bottom pouch foil 60. The pick and place station 54 may be operated, for example, with a stepper motor drive operating a reciprocating pick arm with a vacuum suction cup attached.

A bottom foil unwind 62 provides the bottom pouch foil 60. A top foil unwind 64 provides the bottom pouch foil 66. The bottom and top pouch foils 60,66 provide a foil pouch with the die cut unit inside. The bottom and top foil unwinds 62,64 may use, for example, pneumatically controlled tension clutches for maintaining controlled tension to the pouch foils 60, 66.

The foil pouch is led to a pouch seal station 68 which hermetically seals the top pouch foil 66 to the bottom pouch foil 60 with the die cut unit inside using a seal die. A rubber base may be provided beneath the seal die for forming a seal area around the pouch. The pouch seal station 68 may be operated, for example, with a pneumatic cylinder equipped with a rod-guided counter-levered section for holding the seal die and the rubber base in place.

A foil drive station 70 pulls the pouch foil through the pouch seal station 68 and to a pouch cut station 72. The foil drive station 70 can be driven, for example, by a servo motor. The foil drive station 70 provides registration needed to ensure that the finished units are not located in the seal area of the pouch. If the finished units get caught in the seal area of the pouch, a hermetic seal cannot be achieved by the pouch seal station 68.

The pouch cut station 72 cuts the sealed and registered pouches into a finished pouch system (finished product) and comprises a male die part and a female die part. The die may be operated, for example, with a pneumatic cylinder equipped with a rod-guided counter-levered section for holding the male and female die parts in place.

The finished product falls from underneath the pouch cut station 72 into, for example, a box or a registered conveyor section.

Other embodiments of the method and apparatus for making a non-occlusive patch will be apparent to those skilled in the art from consideration of the specification disclosed herein. It is intended that the specification be considered as exemplary only, with the true scope and spirit of the invention being indicated by the following claims.

What is claimed is:

1. A method of making a patch comprising the steps of:

providing a foam backing having a predetermined porosity;

applying an ointment to the foam backing in a predetermined pattern; and cooling the foam backing prior to application of the ointment to increase thickening and curing of the applied ointment upon contact of the applied ointment with the cooled foam backing.

2. A method as claimed in claim 1, wherein the step of providing a foam backing includes providing an adhesive, providing the foam backing, and laminating the adhesive and the foam backing.

3. A method as claimed in claim 1, wherein the step of applying the ointment to the foam backing includes adjusting a temperature of the ointment to achieve a desired viscosity, and dispensing the ointment through a dispensing head having a predetermined slot pattern.

4. A system for making a patch comprising:

a foam supplier for supplying a foam backing having a predetermined porosity;

a cooling device for cooling the foam backing prior to application of the ointment; and a dispensing device for applying an ointment to the foam backing in a predetermined pattern.

5. A system as claimed in claim 1, wherein the patch is non-occlusive.

6. A system as claimed in claim 4, wherein the foam supplier includes at least one constant tension unwind.

7. A system as claimed in claim 6, wherein the at least one constant tension unwind includes an adjustable spring loaded dancer arm.

8. A system as claimed in claim 6, wherein the foam supplier includes two constant tension unwinds, on supplying an adhesive and the other supplying a foam backing, wherein the adhesive and the foam backing are laminated by a press roller which presses them together.

9. A system as claimed in claim 4, wherein the cooling device comprises a cooling plate.

10. A system as claimed in claim 9, wherein the cooling plate is positioned adjacent to the foam backing.

11. A system as claimed in claim 9, wherein the cooling plate comprises aluminum.

12. A system as claimed in claim 9, wherein the cooling plate abuts the foam backing.

13. A system as claimed in claim 9, wherein a chilled liquid or gas is pumped through the cooling plate.

14. A system as claimed in claim 4, wherein the cooling device comprises an inert gas circulated through a manifold positioned adjacent to the foam backing.

15. A system as claimed in claim 14, wherein the inert gas is nitrogen.

16. A system as claimed in claim 14, wherein the cooling device further comprises a cooling plate.

17. A system as claimed in claim 4, wherein the cooling device comprises an air blower adjacent to the foam backing.

18. A system as claimed in claim 4, wherein the cooling device comprises a refrigeration unit.

19. A system as claimed in claim 4, wherein the ointment contains a medication.

20. A system as claimed in claim 4, wherein the dispensing device includes a dispensing die.

21. A system as claimed in claim 20, wherein the dispensing die has a dispensing head.

22. A system as claimed in claim 21, wherein the dispensing head has a predetermined slot pattern.

23. A system as claimed in claim 20, wherein the dispensing device further includes a metered pump having a temperature control system.

24. A system as claimed in claim 20, wherein the dispensing die dispenses an accurately controlled predetermined pattern of ointment onto the foam backing.

25. A system as claimed in claim 4, wherein the predetermined pattern includes plural lines of droplets of ointment.

26. A system as claimed in claim 25, wherein the lines are crosshatched.

27. A system as claimed in claim 4, wherein the predetermined pattern includes a series of concentric circles.

28. A system as claimed in claim 4, wherein the predetermined pattern includes a series of concentric ovals.

29. A system as claimed in claim 12, wherein the cooling plate cools the foam backing before the dispensing device applies ointment to the foam backing.

30. A system as claimed in claim 28, wherein the cooling plate includes a vertical adjuster which adjusts a height of the foam backing relative to the dispensing device before the dispensing device applies ointment to the foam backing.

* * * * *